United States Patent [19]

Armitage

[11] 4,327,082
[45] Apr. 27, 1982

[54] MASTITIS VACCINATION

[75] Inventor: Rodney E. Armitage, Northcliff, South Africa

[73] Assignee: Adcock-Ingram Laboratories Limited, Johannesburg, South Africa

[21] Appl. No.: 178,217

[22] Filed: Aug. 14, 1980

[30] Foreign Application Priority Data

Jul. 12, 1979 [ZA] South Africa .................. 79/4883

[51] Int. Cl.³ .................. A61K 39/085; A61K 39/00
[52] U.S. Cl. ..................... 424/92; 424/85; 424/88
[58] Field of Search ............... 424/85–87, 424/88, 92

[56] References Cited

U.S. PATENT DOCUMENTS 4,197,290  4/1980  Yoshida .................. 424/92

OTHER PUBLICATIONS

Derwent Abstract of South Africa Patent No. 67/6154, 1968.
Boughton et al., The Veterinary Bulletin, vol. 49, pp. 377–385, 1979.

Primary Examiner—Blondel Hazel
Attorney, Agent, or Firm—Beveridge, DeGrandi & Kline

[57] ABSTRACT

A method of vaccinating a cow against mastitis by administering to the cow an intravaginal anti—mastitis vaccine during the lactation period followed by administering an intracisternal anti-mastitis vaccine to the cow during the dry period. The intravaginal and intracisternal vaccines preferably contain Toxoided Alpha-Toxin, detoxified Leucocidin and an extract of the bacteria *Staphylococcus aureus*.

3 Claims, 1 Drawing Figure

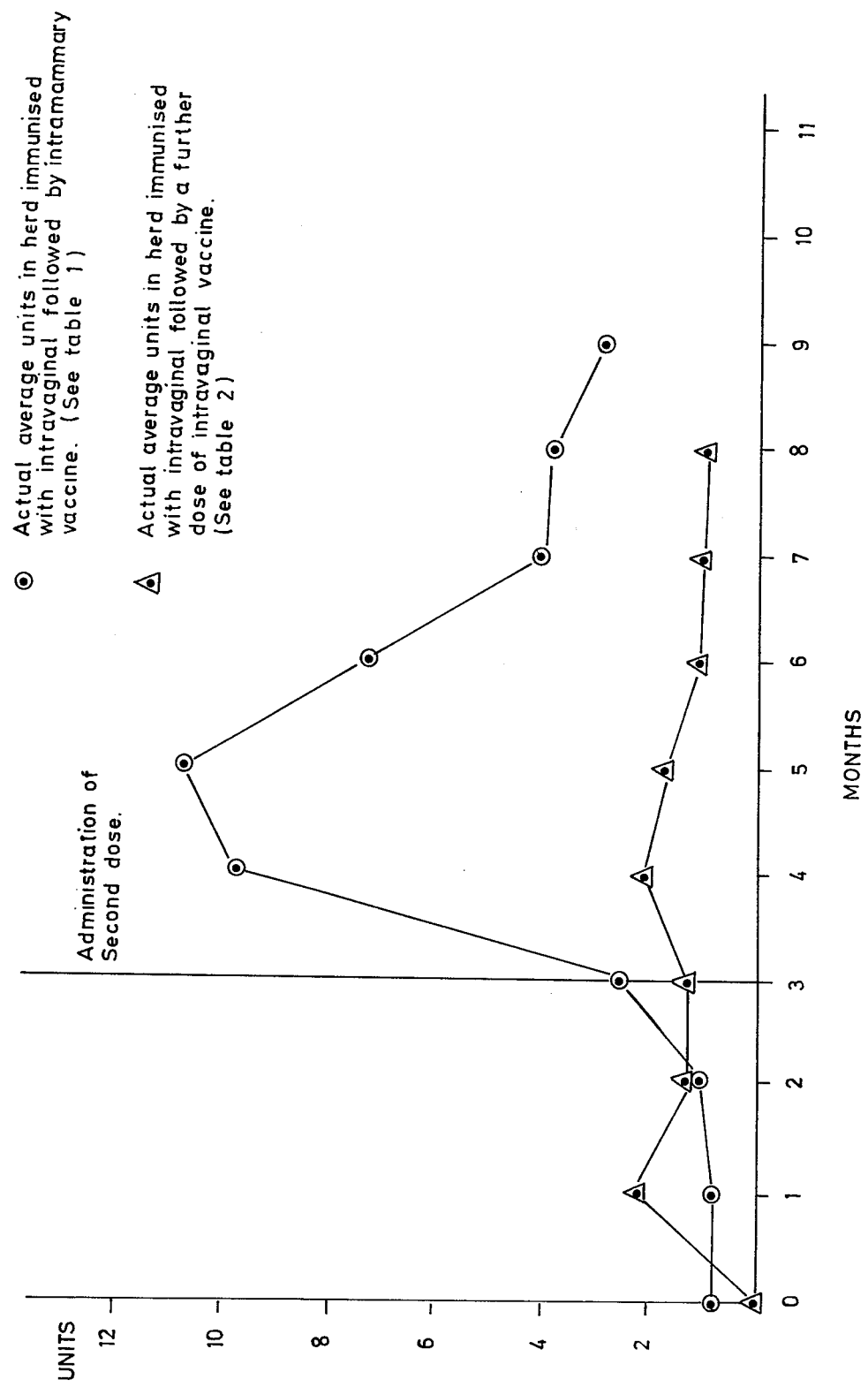

MASTITIS VACCINATION

This invention relates to a method of vaccinating cows against staphylococcal mastitis.

South African Pat. No. 67/6154 describes and claims an anti mastitis vaccine, a method of making the vaccine and a method of administering the vaccine. In particular, the novel method of administration described and claimed is intranasal, intravaginal and intramammary.

It has now been found, and this forms the basis of the present invention, that the combination of an intracisternal (intramammary) vaccine and an intravaginal vaccine produces a synergisic effect.

Thus, the invention provides a method of vaccinating a cow against mastitis by administering an intravaginal vaccine during the lactation period of the cow followed by administering an intracisternal vaccine to the cow during the dry period. Generally, the intravaginal vaccine will not be administered earlier than three months prior to the start of the dry period, i.e. when the udder is involuted. The intracisternal vaccine is typically administered halfway through the dry period.

It has surprisingly been found that the intracisternal vaccine boosted by the intravaginal vaccine causes a synergistic elevation in alphatoxoid antibodies in the blood serum of cows to a level in excess of that achieved by introducing the intravaginal vaccine followed by another such vaccine or an intracisternal vaccine alone.

The intravaginal and intracisternal vaccines contain Toxoided Alpha-Toxin, detoxified Leucocidin and an extract of the bacteria *Staphylococcus aureus*

The individual components may be prepared as follows.

PREPARATION OF DETOXIFIED ALPHA-TOXIN (TOXOID)

Several strains of *Staphylococcus aureus* were plated out and colonies selected for high toxin yield. These strains were cultured in a hydrolized beef with liver extract solution. The culture was centrifuged, formaldehyde added to the supernatant liquid and the mixture was allowed to stand with the formaldehyde content being maintained.

The clear liquid was precipitated by saturation with ammonium sulphate. The substance was purified by redissolving, dialysis and further precipitation.

The final solid substance was dried in a stream of air.

PREPARATION OF DETOXIFIED LEUCOCIDIN

A selected strain of *Staphylococcus aureus* was cultured in a media detailed above. A phenol or formaldehyde solution was added and the mixture centrifuged. The clear solution was precipitated with ammonium sulphate, purified and dried as described above.

PREPARATION OF SURFACE ANTIGENS

Various selected strains of mastitis causing staphylococci were cultured separately in a medium similar to that described above. In addition colonies from Smith's strain was also cultured. Each of the cultures were separately treated with phenol to kill all live organisms followed by extraction in an aqueous phenol solution. The extracts were centrifuged and the clear liquid precipitated with ammonium sulphate with further treatment for purification and drying as previously described. A residual amount of ammonium sulphate was retained in the final dried product to stabilize the final substance against moisture.

Typical vaccine compositions are as follows.

COMPOSITION OF INTRACISTERNAL VACCINE

Each dose contains:

Toxoided Alpha-Toxin: 80 I.U.

Leucocidin (detoxified): 60 I.U.

Somatic Antigens obtained from $10^{10}$ Bacteria *Staphylococcus aureus* to which is added Procaine Penicillin and Neomycin.

The product may be produced without the antibiotic or in combination with other antibiotics in various strengths. The Toxoid/Antigen content may also be varied depending on the antibody response of the immunized animals.

The final product has an aqueous base and may be packed in a suitable container designed for intramammary administration. The product is free of pathogenic organisms.

COMPOSITION OF INTRAVAGINAL VACCINE

Each dose contains:

Toxoided Alpha-Toxin: 250 I.U.

Leucocidin (detoxified): 150 I.U.

Somatic Antigens obtained from $10^{10}$ Bacteria *Staphylococcus aureus*

Experimental trials have shown this combination in the stated strengths to be particularly effective. The individual strengths can be altered, depending on the results obtained from serological evaluations.

The mixed Toxoid/antigens may be formulated into a tablet using excipients which are non-toxic and compatible with the active ingredients. The tablet is administered into the vagina where it forms a depot from which slow absorption takes place.

An example of the invention will now be described with reference to the following Example and FIG. 1.

FIG. 1 compares graphically results obtained using the method of the invention with those obtained using successive intravaginal vaccines.

EXAMPLE 21 (twenty one) cows were immunized intravaginally with the vaccine described above, three to four months before the udder was completely involuted. Approximately four weeks after commencement of the drying off period a dose of intracisternal vaccine (as described above) was introduced into each quarter of the udder.

Blood samples were collected from each animal every month and the serum checked for antibody levels against an International Standard alpha-Toxin.

The results achieved are summarised in what follows:

TABLE 1

| COW NO. | INTRAVAGINAL ADMINISTRATION MONTHS BEFORE INTRAMAMMARY | | | | MONTHS AFTER INTRAMAMMARY APPLICATION | | | | | |
|---|---|---|---|---|---|---|---|---|---|---|
| | 4 | 3 | 2 | 1 | 1 | 2 | 3 | 4 | 5 | 6 |
| 781 | 0 | 0 | 1 | 1 | 20 | 8 | 5 | 4 | 4 | 2 |
| 255 | | | 0 | 1 | 6 | 20 | 7 | 3 | 3 | 2 |
| 783 | 0 | 5 | 2 | 2 | 5 | 4 | 2 | 2 | 2 | 2 |
| 522 | | | 0 | 1 | 3 | 2 | 1 | 0 | 0 | 0 |
| 333 | | 0 | 1 | 1 | 10 | 6 | 4 | 3 | 3 | 2 |
| 437 | | 0 | 1 | 1 | 7 | 2 | 1 | 4 | 4 | 2 |
| 330 | | 0 | 1 | 1 | 17 | 15 | 8 | 6 | 6 | 4 |
| 402 | | | 0 | 1 | 5 | 10 | 4 | 2 | 3 | 1 |
| 346 | | 0 | 1 | 2 | 8 | 20 | 16 | 7 | 4 | 3 |
| 301 | | | 0 | 3 | 20 | 20 | 14 | 5 | 3 | 3 |
| 41 | | 0 | 1 | 5 | 10 | 4 | 3 | 2 | 1 | 1 |
| 16 | | 0 | 4 | 9 | 10 | 14 | 8 | 2 | 5 | 5 |
| 175 | | 0 | 1 | 3 | 12 | 5 | 4 | 5 | 5 | 5 |
| 202 | | 0 | 2 | 1 | 5 | 20 | 18 | 8 | 12 | 4 |
| 168 | | 0 | 2 | 5 | 9 | 8 | 4 | 4 | 2 | 2 |
| 279 | 0 | 2 | 2 | 0 | 20 | 19 | 15 | 5 | 4 | 4 |
| 111 | | | 0 | 1 | 7 | 4 | 3 | 3 | 3 | 3 |
| 193 | | | 0 | 8 | 13 | 7 | 8 | 7 | 7 | 6 |
| 144 | 3 | 4 | 1 | 1 | 6 | 12 | 6 | 3 | 3 | 1 |
| 263 | | 0 | 3 | 3 | 7 | 6 | 4 | 2 | 2 | 2 |
| 113 | | 0 | 2 | 4 | 7 | 19 | 14 | 7 | 6 | 6 |
| TOTAL UNITS ANTIBODY a-Toxoid | 3 | 11 | 25 | 54 | 207 | 225 | 153 | 84 | 82 | 60 |
| AVERAGE | 0,75 | 0,73 | 1,19 | 2,57 | 9,8 | 10,71 | 7,28 | 4,00 | 3,9 | 2,85 |

Intramammary Application

To compare the a toxoid antibody titre in animals immunized with the intravaginal vaccine followed by the intramammary dose, with animals immunized with two administrations of the intravaginal vaccine, a second trial was carried out resulting in the figures shown in Table 2. This comparison was to prove that the anticipated curve (see FIG. 1) was not less than the actual shown in the second trial and also demonstrated the synergistic influence that these two dosage forms had on each other.

TABLE 2

| COW NO. | INTRAVAGINAL ADMINISTRATION MONTHS BEFORE SECOND DOSE | | | | INTRAVAGINAL ADMINISTRATION MONTHS AFTER SECOND DOSE | | | | |
|---|---|---|---|---|---|---|---|---|---|
| | 4 | 3 | 2 | 1 | 1 | 2 | 3 | 4 | 5 |
| 22 | 0 | 4 | 3 | 2 | 1 | 1 | 1 | 1 | 1 |
| 40 | 0 | 2 | 2 | 2 | 2 | 2 | 1 | 1 | 1 |
| 46 | | 0 | 0 | 0 | 0 | 0 | 1 | 1 | 1 |
| 369 | 0 | 1 | 1 | 1 | 3 | 2 | 1 | 1 | 1 |
| 399 | 0 | 0 | 0 | 1 | 8 | 6 | 2 | 1 | 1 |
| 430 | 0 | 2 | 2 | 2 | 2 | 1 | 1 | 1 | 1 |
| 434 | 0 | 1 | 1 | 1 | 1 | 1 | 1 | 1 | 1 |
| 468 | 0 | 8 | 1 | 1 | 0 | 1 | 1 | 1 | 1 |
| TOTAL | 0 | 18 | 10 | 10 | 17 | 14 | 9 | 8 | 8 |
| AVERAGE | 0 | 2,25 | 1,25 | 1,25 | 2,13 | 1,75 | 1,12 | 1 | 1 |

SECOND INTRAVAGINAL DOSE

The points plotted on FIG. 1 are taken from the average reading in units of a toxoid antibodies as shown above in Table 2. A linear to curved estimate is made to establish an anticipated maximum unit level at month 4, 5 and 6

| | MONTH | | |
|---|---|---|---|
| | 4 | 5 | 6 |
| ACTUAL LEVEL INTRAVAGINAL ONLY | 3 | 3,2 | 2,6 |
| ACTUAL LEVEL VAGINAL/INTRAMAMMARY | 9,8 | 11,05 | 7,79 |

The intramammary vaccine in combination with the intravaginal vaccine is synergistic resulting in a 3,3 fold increase in antibody level one month after the combined vaccines had taken effect followed by a 3,5 fold and a 3 fold increase after 2 and 3 months respectively.

I claim:

1. A method of vaccinating a cow against mastitis including the steps of administering to the cow an effective amount of an intravaginal anti-mastitis vaccine during the lactation period followed by administering an effective amount of an intracisternal anti-mastitis vaccine to the cow during the dry period, wherein the intravaginal and intracisternal vaccines contain Toxoided Alpha-Toxin, detoxified Leucocidin and an extract of the bacteria Staphylococcus aureus.

2. A method of claim 1 wherein the intravaginal vaccine is administered not more than three months prior to the start of the dry period.

3. A method of claim 1 wherein the intracisternal vaccine is administered halfway through the dry period.

* * * * *